| United States Patent [19] | [11] Patent Number: 4,942,221 |
| Moinet et al. | [45] Date of Patent: Jul. 17, 1990 |

[54] PROCESS FOR OBTAINING α-AMINO NITRILES AND THEIR APPLICATIONS TO ORGANIC SYNTHESIS

[75] Inventors: Gerard Moinet, Orsay; Thierry Imbert, Noisy le Roi, both of France

[73] Assignee: Albert Rolland S.A., Paris, France

[21] Appl. No.: 86,731

[22] PCT Filed: Nov. 19, 1986

[86] PCT No.: PCT/FR86/00391

§ 371 Date: Aug. 4, 1987

§ 102(e) Date: Aug. 4, 1987

[87] PCT Pub. No.: WO87/02980

PCT Pub. Date: May 21, 1987

[30] Foreign Application Priority Data

Nov. 19, 1985 [FR] France ................................. 85 17214

[51] Int. Cl.$^5$ .................. C07C 253/30; C07C 253/08
[52] U.S. Cl. ...................................... 558/408; 548/505;
558/339; 558/352; 558/378; 558/389; 558/428;
558/430; 558/432; 558/447; 558/452; 558/454

[58] Field of Search ............... 558/408, 389, 447, 339,
558/352, 378, 428, 430, 432, 452; 548/505

[56] References Cited

U.S. PATENT DOCUMENTS

| 3,265,745 | 8/1966 | Seyferth et al. | 558/434 X |
| 3,660,416 | 5/1972 | Vit | 558/440 X |
| 4,517,130 | 5/1985 | Baer | 562/453 X |

FOREIGN PATENT DOCUMENTS 2174186 10/1973 France .
2380256 9/1978 France .

OTHER PUBLICATIONS

Lancaster Synthesis 89, 90, p. 268.

Primary Examiner—Joseph Paul Brust
Attorney, Agent, or Firm—Bierman and Muserlian

[57] ABSTRACT

The present invention relates to the synthesis of nitriles having an amine function on the adjacent carbon.

8 Claims, No Drawings

PROCESS FOR OBTAINING α-AMINO NITRILES AND THEIR APPLICATIONS TO ORGANIC SYNTHESIS

SUMMARY OF THE INVENTION

It relates more especially to a process for preparing α-aminonitrile which consists in transforming a nitrile into its upper homologue bearing an amine function in α-position, by a one-stage process.

Thus, the present invention provides a process for obtaining α-aminonitriles of the general formula I:

$$\begin{array}{c} R' \\ | \\ R-C-CN \\ | \\ NH_2 \end{array} \quad I$$

wherein R represents an aliphatic, aromatic or cyclanic radical, R' represents a hydrogen atom, an unsubstituted or substituted alkyl radical, or an aryl radical, in which an aliphatic, aromatic or cyclanic nitrile of the general formula II $$R-C\equiv N \quad II$$

in which R has the meaning here-above defined, is submitted to the action of a metallic reducing agent, in order to form a metallic imine of the general formula III $$\begin{array}{c} R' \\ | \\ R-C=N-Me(Z)_n \end{array} \quad III$$

wherein R and R' have the meanings previously defined; Me is a metal atom; Z is a lower alkyl radical or a halogen atom, and n is an integer equal to the valence of the metal diminished by one; and the latter is reacted with a cyaniding agent.

In a preferred way, the metallic reducing agent is a metal hydride as an aluminohydride having at least one free hydrogen atom. It may also be an alkylating or arylating reducing agent such as an organomagnesian salt of the formula R'MgX wherein R' is an unsubstituted or substituted alkyl radical, or an aryl radical, or an organozinc salt of the formula HalZnR' wherein Hal represents a halogen atom with the exception of a fluorine atom, and R' has the meaning previously given or organocadminum salt or an organo copper salt. As preferred agent; there may be mentioned disiobutyaluminum hydride, diterbutoxyaluminum hydride or sodium bis (2-methoxyethoxy) aluminum hydride.

The cyaniding agent is selected from the group consisting of trimethylsilyl cyanide, diethylaluminum cyanide, and tributylstannicyanide (Bu)₃Sn-CN. This list is not limiting and other cyaniding agents able to give up a CN group may also be used such, for example, as an alkaline or alkaline-earth metal cyanoborohydride, an alkaline metal cyanide in the presence of a brown Ether, or hydrocyanic acid in solution in an oxygen-bearing solvent, as for Example THF.

The following table gives a comparison between the different reducing agent and the different cyaniding agents.

COMPARISON OF YIELDS OBTAINED BY HYDROCYANATION OF NITRILES

| Nitriles | Cyaniding Agents | | | | | α-aminonitriles |
|---|---|---|---|---|---|---|
| | $(C_2H_5)_2AlCN$ | $(CH_3)_3SiCN$ | $(C_4H_9)_3SnCn$ | HCN/THF | LiCN/DMF | NaCN/DM |
| PhCH₂CN | 65 | 55 / 0 | 24 | 70 | 60 | 60 — PhCH(NH₂)CH₂CN (shown as CH₂-CH(CN)(NH₂)-Ph) |
| PhOCH₂CN | 22 | 27 / 20 | | | | — PhOCH₂CH(CN)NH₂ |
| PhCH=CHCN * | 20 | 33 | | | | — PhCH=CH-CH(CN)NH₂ |
| EtO-CH=CH-CN | | 20 | | | | — EtO-CH(CN)-CH(CN)NH₂ |
| CH₃O-indole-CH₂CN | | 62 / 57 | | 70 | | 50 — CH₃O-indoline-CH₂CH(CN)NH₂ |
| PhCN | | | | | | — PhCH(CN)NH₂ |

A: Yield in % obtained with Diisobutyl aluminum hydride (DIBA)
B: Yield in % obtained with sodium bis(2-methoxyethoxy) aluminum hydride (nitride.^R)
*Reaction carried out at 60° C.

Without limiting the invention, the process of the present invention may be illustrated by the two following reaction schemes (1) Using an aluminohydride as metallic reducing agent:

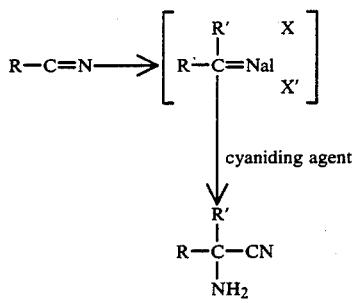

(R'=hydrogen).

(2) Using an organometal halide as alkylating reducing agent

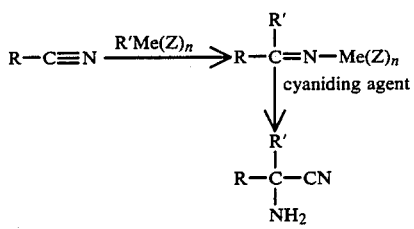

(R'=alkyl or aryl).

In these two schemes, R is a substituted or unsubstituted alkyl radical having from 1 to 30 carbon atoms, a mono-or bi-cyclic aryl radical, an alkenyl radical having from 2 to 30 carbon atoms, a mono- or bi-cyclic hetero-aryl radical; an aryl-alkyl radical in which the alkyl moiety has from 1 to 15 carbon atoms and the aryl moiety may carry from 1 to 3 substituents, an aryloxy-(lower)alkyl radical optionally substituted by one to three substituents on the aryl moiety, or a cycloalkenyl radical having from 4 to 7 carbon atoms lower alkyl.

As much as the invention is concerned, the term lower alkyl means a hydrocarbonic radical having from 1 to 6 carbon atoms, in a straight or branched chain. There may be mentioned as example: butyl, terbutyl, neopentyl, n-hexyl, methyl or ethyl radicals.

When the alkyl radical is substituted, it may carry a group functional towards organometal compound as a halogen atom, or an amino radical as a chain of the formula

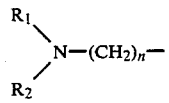

in which $R_1$ and $R_2$ each represent a hydrogen atom, an alkyl radical, an aryl radical or an alkylene chain and n is an integer from 1 to 30. It may also carry a hydroxy, alkoxy or aryloxy substituent in order to form a chain of the formula:

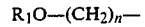

in which $R_1$ is a hydrogen atom, an alkyl radical or an aryl radical and n is as here-above defined. It may also carry a carbonyl substituent or an alkoxy carbonyl substituent previously protected under the form of dioxolan or ortho-ester

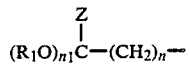

in which $n_1$ is the integer 1 to 2 and Z is an alkyl radical, an oxygen atom or a lower alkoxy radical.

The term lower alkenyl radical means a hydrocarbonic radical having a double bond and containing from 2 to 6 carbon atoms. As alkenyl radical, there may be mentioned for example, allyl, methallyl, but-2-enyl, isopropenyl and 3-methyl-butylenyl radicals.

When R represents a substituted aryl radical, the substituents may be from 1 to 3 halogen atoms, a trifluoromethyl or trifluoromethoxy radical or 1 to 3 lower alkyl or lower alkoxy radicals.

The term aryl (lower) alkyl radical means a monocyclic aryl radical carrying a hydrocarbonic chain having from 1 to 6 carbon atoms in a straight or branched chain. Some examples of such radicals may be benzyl, phenyl-ethyl, α-methylphenyl,ethyl 2,6-dichlorobenzyl and 2,3,5-trimethoxy-benzyl radicals. The term heteroaryl(lower)alkyl radical means a heterocyclic aromatic radical carrying a hydrocarbonic chain having from 1 to 6 carbon atoms. As example of such radicals, there may be mentioned (2-pyridyl)methyl, furyl-ethyl, pyranyl-ethyl, (2-thienyl)methyl and indololylmethyl radicals.

A heteroaryl radical means a cyclic structure having from 4 to 7 links as azetidine, pyrrolidine, piperidine or hexamethyleneimine when this chain is interrupted by one or two hetero-atoms such as a sulfur, or an oxygen atom or an imino group, the resulting cycle may be, for example, tetrahydropyrimidine, tetrahydrooxazine morpholine, thiazine, pyrazolidine or piperazine. These cycles may carry substituents as, for example, lower alkyl, hydroxy(lower)alkyl, pyridyl, unsubstituted or substituted phenyl or pyrimidinyl radicals.

The invention may, futhermore, be performed by the following operating methods which are at the present time, the preferred embodiments:

(1) the imination reaction is carried out in an inert solvent as an aromatic carbide such for example as toluene, xylene, a linear or cyclic ether, such for example as tetrahydrofuran or dioxane.

(2) the imination reaction is performed at low temperature, more particularly within the range of from −30° to +10° C.;

(3) the cyaniding reaction is carried out in the same solvent as the one used for the imination reaction;

(4) the cyaniding reaction is carried out in the absence or in the presence of a Lewis acid as for example: aluminum chloride, zinc chloride, stannichloride or boron-trifluoride;

(5) the cyaniding reaction is carried out in the reaction mixture without isolating previously the imine;

(6) the cyaniding reaction is performed at a temperature within the range of from −20° to +50° C., preferably about 0° C.

As it may be observed, the process according to the invention is characterized by the great simplicity of its carrying out. In a first step, the nitride RCN in solution in an inert solvent is reacted, at low temperature and under an inert atmosphere, with the metallic reducing agent, then after a brief contact, the cyaniding agent is added while stirring. After the usual purification, the α-amino-nitrile is obtained.

The process of the present invention may be used for preparing starting materials of the general formula IV:

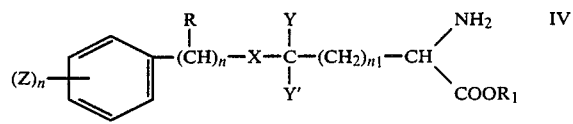

as described in European patent application No. 85401360, 4 of July 4, 1985.

Such amino-acids or amino-esters are obtained starting from α-cyano-amines of the general formula I, either by an acid hydrolysis in a diluted mineral acid, or by an enzymatic hydrolysis, or again by a Pinner reaction giving first an imidolate giving then an α-amino-ester:

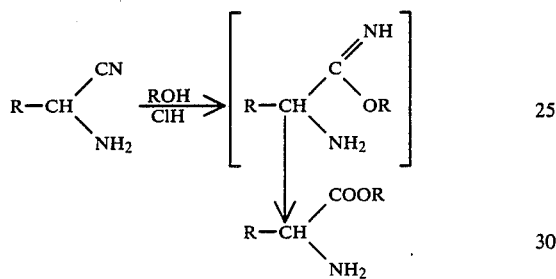

It is also possible to obtain, according to the process of the invention, α-substituted α-cyano-amines which constitute some precious precurors for the synthesis of α-substituted α-amino acids, such for example as α-methyl DOPA or α-fluoroamino acids named suicidal enzymes.

The synthesis scheme is the following:

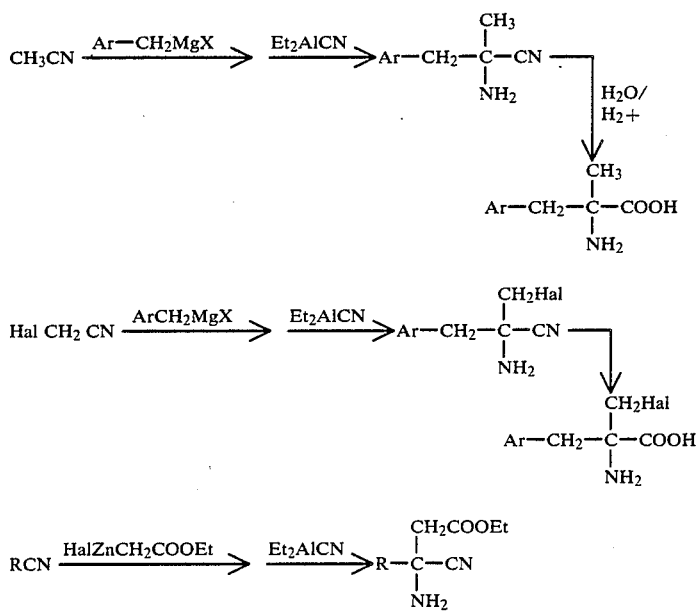

An other interest of the process of the invention consists in the possibility of obtaining a large range of intermediates of synthesis by attack of the nitrile group:

hydrolysis in amino-acid,
aminolysis in amidine,
hydrazinolysis in amindrazone,
attack by hydroylamine in amidoxime of the formula

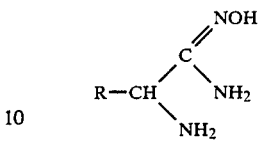

All these compounds are precious intermediates to form after cyclization some hetero-cyclic compounds such as oxazolines, imidazolines, oxadiazoles or triazoles.

An other interest of the process of the present invention consists in the fact that α-cyano-amines of the general formula I may be submitted to an enzymatic hydrolysis to form, preferably an optically active amino-acid. Thus it is possible to access, with a good yield, either to an amino-acid having an antipodal configuration such for example as D-alanine which finds many uses in the synthesis of Enkephaline antibacterial products or enzymatic inhibitors, or to an amino-acid having a natural configuration.

It is possible to access, by the process of the invention, to some amino acids or to some aromatic or hetero-cyclic aminonitriles, which may be substituted or unsubstituted, the isolation of which, in nature, is difficult or uneconomic. Thus, starting from 2-cyanopyridine, there may be obtained 2-(2-pyridyl)-2-cyano amino-methane, which is hydrolyzed in 2-(2-pyridyl)-2-amino-acetic acid.

There may also be obtained, according to the process of the invention, phenylglycine or p-hydroxyphenylglycine which are precious starting materials for making semi-synthetic penicillins.

The following examples describe and illustrate the invention without limiting it.

EXAMPLE 1

Preparation of 2-amino-3-phenoxy-propionitrile (A) First method:

(a) 5 millimoles (0.665 g) of phenoxy-acetonitrile are dissolved in 8 ml of anhydrous toluene at 0° C., under an argon atmosphere 7.5 millimoles of a toluenic solution 1.5 M of diisobutylaluminum hydride (5 ml) are added dropwise, at this temperature. The stirring is maintained for 1 hour at 0° C., then 5.9 ml (1.3 eq) of diethylaluminum cyanide are added. The reaction mixture is stirred for 3 hours at room temperature, then hydrolyzed with 4 ml of methanol and pasty sodium sulfate. After purification by high pressure liquid chromatography on silica, there are obtained 0.182 g of 2-amino-3-phenoxy-propionitrile, in form of a cream-colored solid-state product; M.P. 65° C., yield: 22%.

(b) In accordance with the above method but using trimethylsilyl cyanide instead of diethylaluminum cyanide, there are obtained 0.220 g of 2-amino-3-phenoxy-propionitrile, M.P. 65° C. yield: 27%.

(c) Using the same method, there are also prepared: -4-phenyl-2-amino-butyronitrile, starting from 3-phenyl-propionitrile -2-amino-capronitrile, starting from valeronitrile; -2-amino-3-(cyclohex-1-enyl)-propionitrile starting from cyclohex-1-enyl-acetonitrile, 2-amino-3-(3-benzofuryl-propionitrile starting from (3-benzofuryl)-acetonitrile, 2-amino-3-(3-indolyl) propionitrile, starting from (3-indolyl) acetonitrile.

(B) Second method:

10 millimoles (1.33 g) of phenoxyacetonitrile are dissolved in 10 ml of anhydrous toluene at 0° C., under an argon atmosphere. A solution of vitride (NaH$_2$Al[OCH$_2$-CH$_2$OCH$_3$]$_2$) at 70% in toluene (1,4 ml viz 0.5 eq) in 3 ml of anhydrous toluene is added, dropwise, at this temperature. The stirring is maintained for 1 hour at 0° C., then 2 ml (1.5 eq) of trimethylsilyl cyanide are added. The reaction mixture is maintained at room temperature for 3 hours, while stirring, then hydrolyzed by usual way. After purification by acid base extraction, there are obtained 0.300 g of -2-amino-3-phenoxy propionitrile with a yield of 20%.

EXAMPLE 2

Preparation of 2-amino-2-phenylacetonitrile (A) First method:

(a) 10 millimoles (1.031 g) of benzonitrile are dissolved in 10 ml of anhydrous toluene at 0° C., under an argon atmosphere. 15 millimoles of a toluenic solution 1.5 M of diisobutylaluminum hydride (10 ml) are added dropwise, at this temperature. The reaction mixture is maintained at 0° C. for 1 hour, then 2 ml (1.5 eq) of trimethylsilyl cyanide are added. The stirring is maintained for 3 hours at room temperature, then the mixture is hydrolyzed with 10 ml of methanol, then with pasty sodium sulfate. After purification of α-aminonitrile by an acid-base extraction there are obtained 0.820 g of 2-amino-2-phenyl-acetonitrile, with a yield of 62%.

(b) According to the same way, but using as reducing agent, 0.5 equivalent of a toluenic solutions of Vitride ® of 70% (1.4 ml) diluted in 5 ml of anhydrous toluene (in the place of the toluenic solutions of diisobutylaluminum hydride), there are obtained 0.760 g of 2-amino-2-phenyl-acetontrile, yield 57.5%.

(B) Second method:

(a) 20 millimoles (2.06 g) of benzonitrile are dissolved in 20 ml of anhydrous toluene, at 0° C., under an argon atmosphere. 30 millimoles of a toluenic solution 1.5 M of diisobutylaluminum hydride (20 ml) are added, dropwise, at this temperature. The temperature is maintained at 0° C. for 1 hour, then the reaction mixture is added with 50 ml of a normal solution of sodium cyanide in dimethylformamide. The mixture is maintained at room temperature for 3 hours while stirring, then hydrolyzed with 20 ml of methanol, and with pasty sodium sulfate. After purification of the so obtained α-aminonitrile by high pressure liquid chromatography on silica, with elution by an acid-base extraction, there are obtained 0.350 g of 2-amino-2-phenyl acetonitrile, with a yield of 29%.

(b) by the same way, but using 0.5 equivalent of a toluenic solution by Vitride ® at 70% (2.8 ml) in 6 ml of anhydrous toluenic solution of diisobutylaluminum hydride, there are obtained 1 g of 2-amino-2-phenyl acetonitrile; yield. 38%

EXAMPLE 3

Preparation of 2-amino-3-phenyl-propionitrile (A) First method (a) 10 millimoles (1.17 g) of benzyl cyanide are dissolved in 10 ml of anhydrous toluene at 0° C., under an argon atmosphere. 15 millimoles of 1.5 M toluenic solution of diisobutylaluminum hydride (10 ml) are added, dropwise, at this temperature. The temperature is maintained at 0° C. for one hour, then 13.7 ml (viz 1.5 eq) of diethyl-aluminum cyanide are added. The reaction mixture is stirred for 3 hours while the temperature reaches the room temperature. Then it is hydrolyzed with 10 ml of methanol, and with a slurry of sodium sulfate. After purification of the so-obtained α-aminonitrile, by ethyl acetate/petroleum ether, there are obtained 0.95 g of 2-amino-3-phenyl-propionitrile, in the form of an orange-colored oil, yield: 65%.

(b) According to the same way, but using, as cyaniding agent, trimethylsilyl cyanide, instead of diethylaluminum cyanide, there are obtained after purification by high pressure liquid chromatography on silica, with elution by ethyl acetate/petroleum ether 1/1, 0.80 g of 2-amino-3-phenyl-propionitrile, in the form of an orange-colored oil, with a yield of 55%.

(c) By the same method, but using, as cyaniding agent, tributylstannicyanidle (Bu$_3$SnCN) 0.35 g of 2-amino-3-phenyl-propionitrile are obtained, in the form of an orange-colored oil, with a yield of 24%.

(B) Second method:

(a) 1 millimoles (0.117 g) of benzyl cyanide is dissolved in 1 ml of anhydrous toluene, at 0° C., under an argon atmosphere. 1.5 millimoles of a toluenic solution 1.5 M of diisobutylaluminum hydride (1 ml) are added dropwise at this temperature. The reaction mixture is maintained at 0° C. for 1 hour, then a solution of hydrocyanic acid (in excess) in tetrahydrofuran is added to this mixture, which is then maintained at room temperature for 3 hours, then hydrolyzed with 4 ml of methanol and pasty sodium sulfate. After an acid-base extraction, there are obtained 0.107 g of 2-amino-3-phenyl-propionitrile, in the form of a pale-yellow oil, with a yield of 70%.

(C) Third method (a) 10 millimoles (1.17 g) of benzyl cyanide are dissolved in 10 ml of anhydrous toluene at 0° C., under an argon atmosphere. 15 millimoles of a toluenic solution 1.5 M of diisobutylaluminum hydride (10 ml) are added, dropwise, at this temperature. The mixture is then maintained at 0° C. for 1 hour, and added with 30 ml of a solution 0.5 M (15 millimoles) of lithium cyanide in dimethylformamide. The mixture is maintained at room temperature for 3 hours while stirring, then hydrolyzed by usual way. After an acid-base extraction, 0.92 g of 2-amino-3-phenyl-propionitrile are obtained with a yield of 62%.

(b) By the same way but performing the cyanidation by adding 15 ml of a normal solution of sodium cyanide in dimethylformamide, 0.87 g of 2-amino-3-phenyl-propionitrile are obtained with a yield of 60%.

EXAMPLE 4

Preparation of 2-amino-4-phenyl-3-butene-nitrile (a) 10 millimoles (1.29 g) of cinnamonitrile are dissolved in 150 ml of anhydrous toluene at −70° C., under an argon atmosphere. 15 millimoles of a toluenic solution 1.5 M of diisobutylaluminum hydride (10 ml) are added, dropwise, at −70° C. The stirring is maintained at this temperature for 30 minutes, then 2 ml of trimethylsilyl cyanide are added at −40° C. The stirring is then maintained at −40° C. for 2 hours. The reaction mixture is then hydrolyzed at −20° C. with 10 ml methanol and with pasty sodium sulfate. The so-obtained product is purified by liquid chromatography on silica, in eluting with ethyl acetate/petroleum ether 1/1. There are obtained 0.515 g of purified 2-amino-4-phenyl-3-butene-nitrile; yield 33%.

(b) Using the same way, but replacing trimethylsilyl cyanide by diethylaluminum cyanide there are obtained 0.300 g of purified 2-amino-4-phenyl-3-butene-nitrile, melting at 79° C.; yield 20%.

EXAMPLE 5

Preparation of 2-amino-4-cyano-4-ethoxy-butyronitrile 51.5 millimoles of ethoxy-acrylonitrile are dissolved in 10 ml of anhydrous toluene at 60° C. under an argon atmosphere. 77.25 millimoles of a toluenic solution 1.5 M of diisobutylaluminum hydride (51.5 ml) are added, dropwise, at −60° C. After stirring at this temperature for 45 minutes, 7.7 ml (1.1 eq) of trimethylsilyl cyanide are added to the reaction mixture at −50° C. The latter is maintained at −50° C. for 3 hours while stirring, then hydrolyzed by ammonium chloride then water. After purification of the so-obtained aminonitrile, by liquid chromatography on silica (elution with ethyl acetate/petroleum ether 1/1), 1.7 g of 2-amino-4-cyano-4-ethoxy-butyronitrile are obtained in a form of an orange-colored oil.

EXAMPLE 6

Preparation of 2-amino-3-(5-methoxy-3-indolyl)-propionitrile (a) 21.5 millimoles (4 g) of (5 methoxy-3-inololyl)-acetonitrile are dissolved in 43 ml of anhydrous toluene at 0° C., under an argon atmosphere. 32.25 millimoles of a toluenic solution 1.5 M of diisobutylaluminum hydride (21.5 ml) are added, dropwise, at this temperature. The mixture is maintained at 0° C. for 1 hour while stirring, before it is to be added with 43 ml (1.5 eq) of trimethylsilyl cyanide. The stirring is maintained for 3 hours at room temperature, then the mixture is hydrolyzed with 40 ml of methanol, then pasty sodium sulfate. After purification by an acid-base extraction, 3.28 g of 2-amino-3-(5-methoxy-3-indolyl)-propionitrile were obtained with a yield of 71%.

(b) By the same way, starting from 27 millimoles (5 g) of (5-methoxy-3-indoly)acetonitrile and using an excess of hydrocyanic acid in tetrahydrofuran in the place of trimethylsilyl cyanide, there are obtained, after purification by an acid-base extraction, 5.7 g of 2-amino-3-(5-methoxy-3-indolyl)-propionitrile, with a yield of 70%.

(c) Using the same method starting from 5.4 millimoles (1 g) of (5-methoxy-3-indolyl)-acetonitrile and replacing of cyanising agent by 20 ml of a normal solution of sodium cyanide in dimethylformamide, there are obtained, after purification by an acid-base extraction, 0.50 g of 2-amino-3-(5-methoxy-3-indolyl)-propionitrile with a yield of 43%.

EXAMPLE 7

Preparation of 2-amino-2-benzyl-2-phenoxy-3-propionitrile (A) First Method

To 20 millimoles (2.66 g) of phenoxyacetonitrile in 6 ml of anhydrous ether, is added a solution of 30 millimoles (1.5 e.g.) of benzylmagnesium bromide in 6 ml of anhydrous ether. The mixture sets to a mass and 10 ml of tetrahydrofuran are added. After stirring for 2 hours at room temperature, the reaction mixture is cooled by an ice-bath, then added with 50 ml of a normal solution of sodium cyanide in dimethylformamide. After 2 hours of stirring at room temperature, the mixture is hydrolyzed by 10 ml of methanol then by pasty sodium sulfate. There are obtained 3.45 g of raw product, which purified by high pressure liquid chromatography on silica, with a solution by ethyl acetate/petroleum ether 1/1, give 0.3 g of 2-amino-2-benzyl-3-phenoxy-propionitrile. Yield: 6.3%

(B) Second Method

In a three-necked flask provided with a spectrum and a magnetic stirrer, are introduced 0.0069 g M of phenoxy-acetontrile in 20 ml of anhydrous ether. The mixture is cooled in an ice-bath, then added, under argon, with a solution of benzylmagnesium bromide in ether (0.00759 M or 1.1 eg). The reaction mixture is let rise to room temperature, then the stirring is maintained for 1 hour. The mixture takes a red coloration then sets to a mass. It is then diluted with 5 ml of dry tetrahydrofuran. The flask is cooled in a freezing bath, and then 1.2 ml of trimethylsilyl cyanide (0.009 M or 1.3 eg) are added dropwise. The mixture sets to a mass, and 10 ml of dry toluene are added. The mixture remain heterogenous. It is let rise to room temperature and the stirring is maintained for 2 hours.

Some drops of methanol are added then the excess of reactive agent is destroyed by pasty sodium sulfate. The mixture is filtered and the filtrate is concentrated. The dry residue is taken up with isopropylic ether. A precipitation of a beige produce (weight: 0.4 g) melting at 118° C. is obtained after purification by thin layer chromatography, using a solvent formed with petroleum ether-/ethyl acetate (70/30), the yield is 23%.

The IR spectrum is conformed with the structure Titration of the amine function with perchloric acid, T=97.45%. Titration of the nitrogen atoms: 101.3% NMR of the proton in CDCl$_3$ (TMS reference δ=0).

δ1.96—2H (NH$_2$),
2.99—dd 2H (CH$_2$),
3.96—dd 2H (CH$_2$O),
6.85–7.4 10H aromatic.
This product is new.

The obtained α-amino-propionitriles may be cyclized into heterocyclic compounds. They may also be reduced into β-diamines or submitted to a new operation of amino-cyanuration.

What we claim is:

1. A process for obtaining a α-amino nitrile of the formula

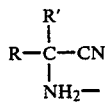   I wherein R is a substituted or unsubstituted alkyl of 1 to 30 carbon atoms, a mono- or bicyclic aryl, an alkenyl of 2 to 30 carbon atoms, an aryl arylalkyl in which the alkyl moiety has from 1 to 15 carbon atoms, an aryloxy lower alkyl unsubstituted or substituted by one to three substituents on the aryl moiety or a cycloalkyl of 4 to 7 carbon atoms and R' is hydrogen or an organo selected from the group consisting of unsubstituted or substituted alkyl of 1 to 3 carbon atoms and a mono- or bicyclic aromatic comprising reacting a nitrile selected from the groups consisting of an alkyl nitrile having 1 to 30 carbon atoms, an alkenyl nitrile of 2 to 30 carbon atoms and an aryl nitrile selected from the group consisting of mono-cyclic aryl nitrile and bicyclic aryl nitrile, an arylalkyl nitrile in which the alkyl moiety has from 1 to 15 carbon atoms, an aryloxy lower alkyl nitrile unsubstituted or substituted by one to three substituents on the aryl moiety or a cycloalkyl nitrile of 4 to 7 carbon atoms comprising reacting a compound of formula

   II wherein R has the above-given meaning with a metallic reducing agent selected from the group consisting of an aluminum hydride, an organo magnesium salt of the formula R' Mg X wherein R' is an unsubstituted or substituted alkyl of 1 to 30 carbon atoms or a mono- or bicyclic aryl, an organozinc salt of the formula

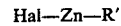

wherein R' is defined as previously given and Hal and X are a halogen atom other than fluorine, organo cadmium salt and organo cooper sale to form a metallic imine of the formula

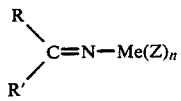   III in which R and R' have the previously-given definitions, Me is a metal atom selected from the group consisting of aluminum, magnesium, zinc, cadmium and copper, Z is lower alkyl or halogen and n is an integer equal to the valence of the metal less one, reacting the latter with a cyaniding agent selected from the group consisting of methylsilyl cyanide, diethylaluminum cyanide, tributylstannicyanide and alkali- or alkaline-earth metal cyanoborohydride, an alkali metal cyanide in the presence of a Crown Ether and hydrocyanic acid in solution in an oxygen-bearing solvent and recovering the corresponding α-amino nitrile of formula I.

2. A process according to claim 1 in which the metallic reducing agent is an aluminum hydride having at least one free hydrogen atom.

3. A process according to claim 1 in which the metallic reducing agent is diisobutylaluminum hydride, diterbutoxyaluminum hydride or sodium bis (2-methoxyethoxy) aluminum hydride.

4. A process according to claim 1 in which the metallic reducing agent is an alkylating or arylating agent selected from the group consisting of organomagnesium salts, organocadmium salts, organozinc salts and organocopper salts.

5. A process according to claim 1 in which the cyaniding agent is selected from the group consisting of diethylaluminum cyanide, trimethylsilyl cyanide, tributylstannic cyanide, an alkaline metal cyanide or hydrocyanic acid.

6. A process according to claim 1 in which the two reactions are carried out successively, in the same reaction mixture.

7. A process according to claim 1, in which the two reactions are carried out at low temperature and under an inert gas atmosphere.

8. A process according to claim 1 for preparing an α-aminonitrile selected from the group consisting of 2-amino-3-phenoxy-propionitrile, 2-amino-2-phenylacetonitrile, 2-amino-3-phenyl-propionitrile, 2-amino-4-phenyl-3-butene-nitrile, 2-amino-4-cyano-4-ethoxy-butyronitrile, and 2-amino-2-phenyl-3-phenoxy-propionitrile and 2 amino-2-benzyl-3-phenoxy-proponitrile.

* * * * *